United States Patent [19]

Lo

[11] Patent Number: 4,723,031

[45] Date of Patent: Feb. 2, 1988

[54] PROCESSES FOR SYNTHESIZING SUBSTITUTED AND UNSUBSTITUTED AMINOACETATE ESTERS

[75] Inventor: William C. Lo, Suisun, Calif.

[73] Assignee: Chevron Research Company, San Francisco, Calif.

[21] Appl. No.: 644,594

[22] Filed: Aug. 27, 1984

[51] Int. Cl.$^4$ ............................................. C07C 101/28
[52] U.S. Cl. ........................................ 560/22; 560/38; 560/39; 560/155; 560/172
[58] Field of Search ................... 560/38, 39, 22, 172, 560/155; 562/575; 564/291

[56] References Cited

U.S. PATENT DOCUMENTS 3,816,533  6/1974  Brandstrom et al. ............... 564/280

FOREIGN PATENT DOCUMENTS

| 1008308 | 5/1957 | Fed. Rep. of Germany | 560/38 |
| 58-222055 | 12/1983 | Japan | 562/575 |
| 6515522 | 5/1967 | Netherlands | 562/575 |
| 1221799 | 2/1971 | United Kingdom | 562/575 |
| 164611 | 10/1964 | U.S.S.R. | 562/575 |

OTHER PUBLICATIONS

Noller, *Chemistry of Organic Compounds,* 2nd ed., 1957, p. 303.
Migrdichian, *Organic Synthesis,* vol. 1, 1957, pp. 275, 305, 308.
Fischer, *Chemisches Berichte,* vol. 37, 1904, pp. 2486-2499.
Slimmer, *Chemisches Berichte,* vol. 35, 1902, pp. 400-411.
Nencki, *Chemisches Berichte,* vol. 16, 1883, pp. 2827-2828.
Chadwick et al, *J. Am. Chem. Soc.,* vol. 63, 1941, pp. 2427-2431.
Orten et al, *J. Am. Chem. Soc.,* vol. 53, 1931, pp. 2797-2799.
Organic Synthesis, vol. I, John Wiley & Sons Inc., pp. 23-25; 153-154 (1941).

*Primary Examiner*—Howard T. Mars
*Assistant Examiner*—Bruce D. Gray
*Attorney, Agent, or Firm*—S. R. La Paglia; R. C. Gaffney; L. S. Squires

[57] ABSTRACT

Process for preparing certain substituted and unsubstituted aminoacetate esters. The esters can be used as intermediates for preparing herbicidal products.

14 Claims, No Drawings

4,723,031

PROCESSES FOR SYNTHESIZING SUBSTITUTED AND UNSUBSTITUTED AMINOACETATE ESTERS

BACKGROUND OF THE INVENTION

This invention relates to processes for preparing substituted and unsubstituted aminoacetate esters. The products of my process are useful as intermediates for useful products. The intermediates produced by my process are especially useful as intermediates for 5-amino-5-oxo-4-(3-substituted phenyl)-4-pyrroline type herbicides.

The preparation of the aminoacetate ester of 2-phenylsarocine is described in J. Organic Chem. Chem. Vol. 29, p. 2764 (1964).

U.S. Pat. No. 3,577,433 is directed to a process for preparing a very broad genus of compounds having the formula:

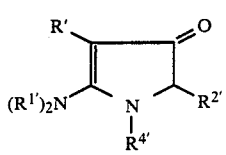

wherein
$R^{1\prime}$ is a hydrocarbon group, such as alkyl, cycloalkyl, aryl, arylalkyl, alkaryl, optionally substituted with groups that are free of reactive hydrogen or $(R^{1\prime})_2$ together with the nitrogen group can form a heterocycle;
$R'$ is as defined for $R^1$ or a substituted amino; and $R^{2\prime}$ and $R^{4\prime}$ are independently hydrogen, alkyl, aryl, cycloalkyl, aralkyl, alkaryl, etc.

Tetrahedron, Vol. 25, 5721-32 (1969); CA:v 72:43329t discloses the preparation of 1,4-diphenyl-3-oxo-5-dimethylamino-pyrroline. Organic Chemistry Vol. 41, pp. 390-2, discloses the preparation of 1-ethyl-2-(2-carboxyphenyl)-3-oxo-4-phenyl-pyrroline. Based on Chem. Abstracts Vol. 92:41753r, Russian patent document SU No. 687070 discloses the preparation of 1,4-diphenyl-3-oxo-5-aminopyrroline and the corresponding 2-methyl, ethyl and phenyl derivatives thereof and Chem. Abstracts Vol. 89:163331 describes a paper by Dopov. of the Akad. Nauk. Ukr. RSR, in Ser. B. Geol., Khim. Biol Nauki, Vol. (7), pp. 619-21 as disclosing the preparation of 1,4-diphenyl-2,2-dimethyl-3-oxo-4-aminopyrroline. Japanese patent document 69/5222 (1969) - Chem. Abstracts Vol. 70:115004S discloses the preparation of 1-methyl-3-oxo-4-phenyl-5-aminopyrroline. British Pat. No. 1,521,092, discloses the preparation of certain 3-phenyl-5-substituted-4(1H)-pyrid-ones or -thiones as herbicides.

SUMMARY OF THE INVENTION

The present invention provides improved processes for preparing certain substituted amino-arylacetate esters, characterized by Formula C on page 3 hereinbelow. Such compounds are especially useful in the preparation of herbicides.

In contrast to the prior art processes for preparing aminoacetate esters, the present process is a short, relatively simple, two-phase synthesis which yields a crude product which can be used directly in further synthetic procedures without purification. Moreover, the process generally provides improved yields and generally uses starting materials which are readily commercially available and relatively inexpensive. The present process is especially easy to use as compared with the usual preparation of aminoacetate esters via the reaction aldehydes with cyanides followed by reaction with amines.

The present process comprises reacting the corresponding substituted or unsubstituted bromoacetate ester with an ammonium salt in a two-phase liquid-liquid reaction medium comprising water and a water immiscible inert organic solvent in the presence of a transfer agent capable of transferring hydrophilic ions into liquid lipophilic organic mediums.

FURTHER DESCRIPTION OF THE INVENTION AND THE PREFERRED EMBODIMENTS

In greater detail, the present process can be schematically represented by the following overall reaction equation:

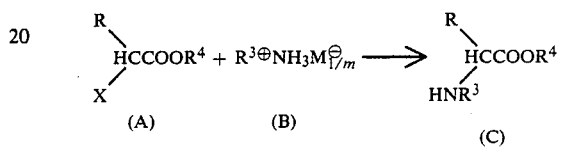

wherein
$M\ominus$ is an anion, preferably a halide; and m is its valence;
X is chloro, bromo, or iodo, preferably bromo; and
R is hydrogen; lower alkyl; lower alkenyl; fluoroalkyl having 1 through 4 carbon atoms and 1 through 3 fluoro atoms; fluoroalkenyl having 2 through 4 carbon atoms and 1 through 3 fluoro atoms; aryl, having 6 through 10 carbon atoms, preferably phenyl; naphth-1-yl; 4-fluorophenyl; 2,6-difluorophenyl; benzyl, naphth-1-ylmethylene; 2-halobenzyl; 2-lower alkylbenzyl; 3-halobenzyl; 3-lower alkylbenzyl; substituted phenyl having the formula:

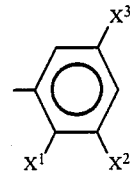

wherein one of $X^1$, $X^2$ or $X^3$ is lower alkyl, lower alkoxy, halo, nitro, or haloalkyl having 1 through 3 carbon atoms and 1 through 3 halo atoms independently selected from the group of fluoro, chloro, bromo or iodo; $X^2$ or $X^3$ is hydrogen, lower alkyl, lower alkoxy, halo, nitro, or haloalkyl, as defined hereinabove, and the other of $X^1$, $X^2$ or $X^3$ is hydrogen;
$R^3$ is methyl or ethyl; and
$R^4$ is lower alkyl.

In accordance with the present invention this process is conducted as a phase transfer reaction by contacting Compound A with a quaternary ammonium salt. (Compound B) in water and a water immiscible inert organic solvent and a phase transfer agent under reactive conditions. Preferably, the reaction is also conducted in the presence of a weak base, for example, sodium bicarbonate. The weak base serves to enhance the reaction by liberating low concentrations of $R^3$ amine for reaction with the bromoester (A).

This process is typically conducted at temperatures in the range of about from 0° to 100° C., preferably, 40° to 45° C., for about from 1 to 60 hours, preferably 18 to 48 hours using about from 1 to 10 moles, preferably 3 to 4 moles of the ammonium salt and 1 to 10 moles, preferably 5 to 6 mole equivalents of weak base and 0.05 to 1 mole equivalents, preferably 0.05 to 0.1 mole equivalents of phase transfer agent per mole of Compound A. Generally, in the case where R is aryl or substituted aryl, shorter reaction times can be used typically 1 to 36 hours, preferably 18 to 36 hours. Whereas, in the other case (e.g., is alkyl, benzyl, etc.) typical reaction times of about from 20 to 60 hours, preferably 24 to 48 hours, are used.

Suitable inert water immiscible organic solvents which can be used include, for example, chloroalkanes, methylene chloride, chloroform, 1,2-dichloroethane, and trichloroethane; toluene, and the like and compatible mixtures thereof. Typically about from 1 to 3, preferably 1.5 to 2 liters of inert organic solvent are used per mole of Compound A. Generally, a water to immiscible solvent volume ratios of about from 1:10, preferably 1 to 15 is used.

The phase transfer agent helps to solubilize the salts (amine salt and $NaHCO_3$ salt) in the organic phase, thus liberating the free amines to react with the alphabromo ester.

Suitable phase transfer agents which can be used are compounds which transfer hydrophilic ions into liquid lipophilic organic mediums and include benzyl triethylammonium chloride, methyl trioctylammonium chloride, tetrabutyl ammonium chloride, tetrabutyl ammonium bromide and the like. Very good results have been obtained using benzyl triethylammonium chloride as the phase transfer agent Suitable weak bases which can be used include, for example, sodium bicarbonate, potassium bicarbonate, lithium bicarbonate, sodium hydrogen phosphate, potassium hydrogen phosphate and the like.

As before mentioned, the product of my process, i.e. Compound C., is generally used as an intermediate to prepare other products. Thus, the selection of the appropriate starting material (A) is generally based on the R group desired in the final product. The $R^4$ moiety, although carried through to the intermediate product (C) is generally not carried through to the final product. Thus, selection of the appropriate ester (i.e., $R^4$) moiety is generally made on the basis of process convenience, availability and cost. Hence, typically, Compound A will be a simple lower alkyl (e.g., methyl) ester. Although in principle $R^4$ can be any group so long as it does not interfere with the present process or the use of product C as an intermediate.

Similarly, the selection of the ammonium salt will be based on the $R^3$ group desired in the final product whereas any $M\theta$ anion can be used which does not interfere with the present reaction and generally will be selected on the basis of process convenience, cost and availability. Suitable $M\theta$ anions include, for example, chloride, bromide, sulfate, fluoroborate, fluoride, and the like.

The ammonium salts of Formula B are known compounds and can be prepared by known procedures or obvious modifications thereof.

The compounds of Formula A wherein R is hydrogen, lower alkyl, lower akenyl, fluoroalkyl, fluoroalkenyl, benzyl, naphth-1-ylmethene or substituted benzyl can be conveniently prepared via the general procedure described in Organic Synthesis Vol. 4, p. 608 (1963) using the appropriate starting materials and solvents.

The compounds of Formula A wherein R is aryl or substituted aryl can be conveniently prepared via halogenation (e.g. bromination). This procedure can be schematically represented by the following overall reaction equation:

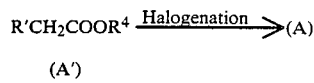

(A')

Wherein R, is aryl or substituted aryl and $R^4$ are as defined hereinabove.

The halogenation can be conveniently effected by treating compound (A') with N-halosuccinimide (e.g., N-bromosuccinimide) in the presence of a suitable catalyst and preferably in an inert organic solvent.

Typically the halogenation is conducted at temperatures in the range of about from 0° to 100° C., preferably 75° to 77° C. for about from 1 to 10 hours, preferably using about 1 to 2 moles, preferably 1 to 1 moles, of N-halosuccinimide and about 0 to 1, preferably 0.05 to 0.1 mole of catalyst per mole of compound A'. Suitable catalysts which can be used include, for example, benzoyl peroxide, di-t-butylperoxide, azobisisobutyronitrile, and the like. Suitable solvents which can be used include, for example, carbon tetrachloride, chlorobenzene, 1,2dichloroethane, tetrachloroethylene, methylene chloride, and the like and compatible mixtures thereof.

The starting materials of Formula (A') are generally known compounds and can be prepared by known procedures or obvious modifications thereof (e.g., substitution of appropriate starting materials, solvents, etc.). Note, for example, Org. Syn. Coll., Volume 1, p. 270 (1941).

As before mentioned, the compounds of Formula C are useful as intermediates for other useful compounds. For example, the compounds of Formula C can be used as intermediates to prepare herbicides and plant growth regulating agent by the procedures described in the commonly assigned copending application of C. E. Ward Ser. No. 645,452 filed 8/27/84 now Pat. No. 4,643,762 filed on even date herewith and hereby incorporated by reference in its entirety. The process described in the Ward application can be represented by the following overall reaction equation.

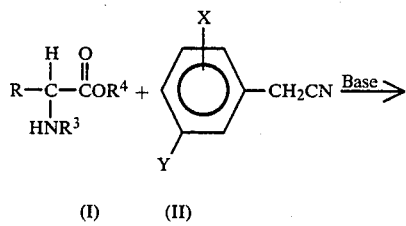

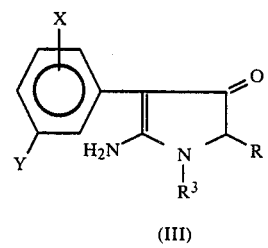

wherein R, $R^3$ and $R^4$ are as defined hereinabove; and X is hydrogen, lower alkyl, lower alkoxy, halo, nitro, or trifluoromethyl and can be at any available position on the phenyl ring; and Y is alkyl, having 3 or 4 carbon atoms; alkoxy, having 3 or 4 carbon atoms, halo, haloalkoxy having 1 through 3 carbon atoms and 1 through 3 halo atoms, haloalkylthio, having 1 through 3 carbon atoms and 1 through 3 halo atoms, or trifluoromethyl.

This process can be conveniently effected by contacting Compound (I) with Compound (II), and a strong base (e.g. sodium methoxide, sodium ethoxide), preferably in an inert organic solvent.

Typically, this process is conducted at temperatures in the range of about from 0° to 100° C., preferably 75° to 85° C. for about from 5 to 36 hours, preferably 18 to 24 hours, using about from 1 to 10, preferably 1 to 1.2 moles of Compound (I) per mole of Compound (II). Suitable inert organic solvents which can be used include, for example, lower alkanols (e.g. methanol, ethanol, propanol, etc.); tetrahydrofuran; dimethoxyethane; dioxane; and the like, and compatible mixtures thereof.

Suitable strong bases which can be used include, for example, alkali metal alkanolates, for example, sodium methoxide, sodium ethoxide, potassium ethoxide, sodium hydride, potassium hydride, and the like. The strong base should preferably be one which does not yield water as a by-product in this reaction system.

Suitable inert solvents which can be used include, for example, lower alkanols (for example, methanol, ethanol, and propanol) tetrahydrofuran, dimethoxyethane, dioxane, and the like, and compatible mixtures thereof. Conveniently, the alkali metal alkanolate is prepared in situ by reacting an alkali metal with excess alkanol which in turn serves as solvent for the above reaction.

The starting materials of Formula (II) are generally known materials and can be prepared by known procedures, or obvious modifications thereof (i.e., substitution of appropriate starting materials). The preparation of Compound (II) is for example described in Org. Syn. Coll., Volume 1, 107 (1941).

General Process Conditions

In the above-described processes, it is generally preferable to separate the respective products before proceeding with the next step in the reaction sequence, except where described as an in situ step or unless otherwise expressly stated. These products can be recovered from their respective reaction product mixtures by any suitable separation and purification procedure, such as, for example, recrystallization and chromatography. Suitable separation and purification procedures are, for example, illustrated in the Examples set forth hereinbelow.

Generally, the reactions described above are conducted as liquid phase reaction and hence pressure is generally not significant except as it affects temperature (boiling point) where reactions are conducted at reflux. Therefore, these reactions are generally conducted at pressures of about from 300 to 3,000 mm of mercury and conveniently are conducted at about atmospheric or ambient pressure.

It should also be appreciated that where typical or preferred process conditions (e.g., reaction temperatures, times, mole ratios of reactants, solvents, etc.) have been given, that other process conditions could also be used. Optimum reaction conditions (e.g., temperature, reaction time, mol ratios, solvents, etc.) may vary with the particular reagents or organic solvents used but can be determined by routine optimization procedures.

Where optical isomer mixtures are obtained, the respective optical isomers can be obtained by conventional resolution procedures. Geometric isomers can be separated by conventional separation procedures which depend upon differences in physical properties between the geometric isomers.

Definitions

As used herein the following terms have the following meanings unless expressly stated to the contrary:

The term "lower alkyl" refers to both straight and branched-chain alkyl groups having a total of from 1 through 6, preferably 1 through 4, carbon atoms and includes primary, secondary and tertiary alkyl groups. Typical lower alkyls include, for example, methyl, ethyl, n-propyl, isopropyl, n-butyl, t-butyl.

The term "lower alkenyl" refers to alkenyl groups having 2 through 6, preferably 2 through 4, carbon atoms and includes, for example, vinyl, 1-propenyl, 2-propenyl, 1-methylvinyl, 1-butenyl, 2-methylprop-1-enyl and the like.

The term "halo" refers to the group of fluoro, chloro, bromo and iodo.

The term "aryl" refers to aryl groups having 6 through 10 carbon atoms and includes, for example, phenyl, naphthyl, indenyl, and the like. Based on the herbicidal activity of the herbicidal products described in the aforementioned application of Carl E. Ward, the aryl group is preferably phenyl, naphth-1-yl or inden-1-yl.

The term "arylalkylene" refers to the group $ArR^5$— wherein Ar is aryl and $R^5$ is alkylene having 1 through 4 carbon atoms and includes both straight-chained and branched-chained alkylenes, for example, methylene, ethyl ($—CH_2CH_2—$), 1-methylethyl ($—CH_2(CH_3)CH_2—$), and propyl ($—(CH_2)_3—$).

The term "substituted aryl" refers to aryl groups substituted with from 1 through 3 substituents independently selected from the group of lower alkyl, lower alkoxy, halo, nitro and haloalkyl having 1 through 3 carbon atoms and 1 through 3 halo atoms.

The term "substituted arylalkylene" refers to the group having the formula $Ar'R^5$- where Ar' is substituted aryl and $R^5$ is alkylene having 1 through 4 carbon atoms and can be straight chained or branched.

The term "3-oxo-4-pyrroline" refers to the group having the formula:

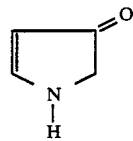

The term "compatible salts" refers to salts which do not significantly alter the herbicidal properties of the parent compound. Suitable salts include cation salts such as, for example, the cation salts of lithium, sodium, potassium, alkali earth metals, ammonia, quaternary ammonium salts, and the like.

The term "room temperature" or "ambient temperature" refers to about 20°–25° C.

Utility of the Compounds of Formula III

As described in the aforementioned Ward application, the compounds of Formula (III) exhibit very good pre-emergence herbicidal activity and to a lesser extent also exhibit post-emergence herbicidal activity.

Generally, for post-emergent applications, the herbicidal compounds are applied directly to the foliage or other plant parts. For pre-emergence applications, the herbicidal compounds are applied to the growth medium, or prospective growth medium, for the plant. The optimum amount of the herbicidal compound or composition will vary with the particular plant species, and the extent of plant growth, if any, and the particular part of the plant which is contacted and the extent of contact. The optimum dosage can also vary with the general location, or environment (e.g., sheltered areas such as greenhouses compared to exposed areas such as fields), and type and degree of control desired. Generally, for both pre- and post-emergent control, the present compounds are applied at rates of about from 0.02 to 60 kg/ha, preferably about from 0.02 to 10 kg/ha.

Also, although in theory the compounds can be applied undiluted, in actual practice they are generally applied as a composition or formulation comprising an effective amount of the compound(s) and an acceptable carrier. An acceptable or compatible carrier (agriculturally acceptable carrier) is one which does not significantly adversely affect the desired biological effect achieved by the active compounds, save to dilute it. Typically, the composition contains about from 0.05 to 95% by weight of the compound of Formula (III) or mixtures thereof. Concentrates can also be made having high concentrations designed for dilution prior to application. The carrier can be a solid, liquid, or aerosol. The actual compositions can take the form of granules, powders, dusts, solutions, emulsions, slurries, aerosols, and the like.

Suitable solid carriers which can be used include, for example, natural clays (such as kaolin, attapulgite, montmorillonite, etc.), talcs, pyrophyllite, diatomaceous silica, synthetic fine silica, calcium aluminosilicate, tricalcium phosphate, and the like. Also, organic materials, such as, for example, walnut shell flour, cotton-seed hulls, wheat flour, wood flour, wood bark flour, and the like can also be used as carriers. Suitable liquid diluents which can be used include, for example, water, organic solvents (e.g., hydrocarbons such as benzene, toluene, dimethylsulfoxide, kerosene, diesel fuel, fuel oil, petroleum naphtha, etc.), and the like. Suitable aerosol carriers which can be used include conventional aerosol carriers such as halogenated alkanes, etc.

The composition can also contain various promoters and surface-active agents which enhance the rate of transport of the active compound into the plant tissue such as, for example, organic solvents, wetting agents and oils, and in the case of compositions designed for pre-emergence application agents which reduce the leachability of the compound or otherwise enhance soil stability.

The composition can also contain various compatible adjuvants, stabilizers, conditioners, insecticides, fungicides, and if desired, other herbicidally active compounds.

At reduced dosages the compounds of the present invention also exhibit plant growth regulating activity and can be used to alter the normal growth pattern of green plants.

The compounds of Formula (III) can be applied as plant growth regulators in pure form, but more pragmatically, as in the case of herbicidal application, are applied in combination with a carrier. The same types of carriers as set forth hereinabove with respect to the herbicidal compositions can also be used. Depending on the desired application, the plant growth regulating composition can also contain, or be applied in combination with other compatible ingredients such as desiccants, defoliants, surface-active agents, adjuvants, fungicides, and insecticides. Typically, the plant growth regulating composition will contain a total of about from 0.005 to 90 wt. % of the compound(s) of Formula (III) depending on whether the composition is intended to be applied directly or diluted first.

Additional details concerning the herbicidal properties of the compounds of Formula III can be had by reference to the application of Carl E. Ward (O-447) filed on even date herewith, which description is hereby incorporated by reference.

A further understanding of the invention can be had in the following non-limiting Preparation and Examples. Wherein, unless expressly stated to the contrary, all temperatures and temperature ranges refer to the Centigrade or Celsius system and the term "ambient" or "room temperature" refers to about 20°–25° C. The term "percent" or "%" refers to weight percent and the term "mole" or "moles" refers to gram moles. The term "equivalent" refers to a quantity of reagent equal in moles, to the moles of the preceding or succeeding reactant recited in that example in terms of finite moles or finite weight or volume. Where given, proton-magnetic resonance spectrum (p.m.r. or n.m.r.) were determined at 60 mHz, signals are assigned as singlets (s), broad singlets (bs), doublets (d), double doublets (dd), triplets (t), double triplets (dt), quartets (q), and multiplets (m); and cps refers to cycles per second. Also where necessary examples are repeated to provide additional starting material for subsequent examples.

EXAMPLES

Example 1

Methyl Bromo-Phenylacetate

In this example, a mixture containing 5.93 g of N-bromosuccinimide, 5.0 g of methyl phenylacetate; and a catalytic amount (about 0.1 g) of benzoyl peroxide in 50 ml of carbon tetrachloride was warmed to reflux and then refluxed for about 12 hours. The mixture was then cooled to about 0° C. and filtered. The filtrate was concentrated by evaporation under vacuum affording 7.1 g of the title compound as an oil.

Example 2

Methyl Methyamino-phenylacetate

In this example a mixture containing 30.7 g of methyl bromo-phenylacetate, 36.2 g of methyl ammonium chloride (i.e. $CH_3NH_3Cl$); 3.0 g of benzyltriethylammonium chloride and 67.5 g of sodium bicarbonate in about 300 ml of methylene chloride (*and about 25 ml of water*) was warmed to refluxed and refluxed for about 18 hours. The mixture was then cooled and washed three times with water, dried over magnesium sulfate and concentrated by vacuum evaporation affording 17.1 g of the title compound as an oil.

Similarly, by applying the same procedure using appropriate reaction times but replacing methyl bromophenylacetate with methyl 2-bromo-naphth-1-ylacetate; methyl bromo-naphth-1-ylmethylene; methyl 2-bromo-3-fluorophenyl; methyl bromo-(3-trifluoromethylphenyl)acetate; methyl bromo-(2-methoxyphenyl)acetate; methyl bromo-(2-bromophenyl)acetate; methyl bromo-(3-methylphenyl)acetate; methyl bromo-(2-chloro-3-fluorophenyl)acetate; methyl bromo-(3-nitrophenyl)acetate; methyl bromo-(2,5-dimethylphenyl), methyl bromo-(2- methoxy-3-methylphenyl)acetate); methyl 2-bromo-proprionate; methyl 2-bromo-3-butenate; methyl bromo-3-fluoropropionate; methyl 2-bromo-3-butenate; methyl 2- bromo-4-fluoro-3-butenate and methyl bromo-benzylacetate; the corresponding methylamino carboxy esters can be prepared. For example, methyl methylamino-naphth-1-ylacetate; methyl methylamino-naphth-1-ylmethyleneacetate; methyl methylamino-3-fluorophenylacetate; methyl methylamino-3-trifluoromethylphenylacetate; methyl methylamino-2'-methoxyphenylacetate; methyl methylamino-2'-bromophenylacetate; methyl methylamino-3-methylphenylacetate; methyl methylamino-2'-chloro-3-fluorophenylacetate; methyl methylamino-3-nitrophenylacetate; methyl methylamino-2',5-dimethylphenylacetate; methyl methylamino-2-methoxy-3-methylphenylacetate; methyl 2-methylaminoproprionate; methyl 2-methylaminobutyrate; methyl 2-methylamino-3-fluoropropionate; methyl 2-methylamino-3-butenate; methyl 2-methylamino-4-fluoro-3-butenate; and methyl 2-methylamino-benzylacetate.

(The bromoester starting materials can be prepared by applying the procedure of Example 1 hereinabove or the appropriate procedure described in A. I. Vogel "Practical Organic Chemistry", 3rd Ed., p. 429 (1956) or Organic Synthesis Vol. 4, p. 608 (1963) to the appropriate starting materials and in some instances are commercially available.) The corresponding chloroesters and iodoesters can also be prepared in the same manner and used in the above procedures, but are less preferred.

Similarly, by following the same procedure but respectively using ethylammonium chloride in place of methylammonium chloride, the corresponding ethylamino homologs of the above compounds can be prepared, for example, methyl ethylamino-phenylacetate.

Example 3

1-Methyl-2-phenyl-3-oxo-4-(3-trifluoromethylphenyl)-5-amino-4-pyrroline

This example illustrates a method according to the aforementioned Ward application for preparing herbicidally active compounds.

In this example, sodium ethoxide was prepared by mixing 3.0 g of metallic sodium with 100 ml of absolute ethanol. After the evolution of hydrogen stopped, a mixture containing 16.0 g of (3-trifluoromethylphenyl)-acetonitrile and 17.1 g of methyl methylamino-phenylacetate was added dropwise to the sodium ethoxide-ethanol mixture. The resulting mixture was then refluxed overnight (about 16 hours) and then cooled to room temperature. The mixture was then added to 300 ml of water and extracted with diethyl ether. The diethyl ether extract was filtered to remove precipitate. The filtrate was concentrated by evaporation affording a solid. This solid was then triturated in diethyl ether/petroleum ether. The diethyl ether/petroleum ether was then removed from the solid.

The solid was washed several times with diethyl ether/petroleum ether and then dried overnight affording 6.2 g of the title compound.

Similarly, by applying the above procedure but using the corresponding methyl methylamino esters in place of methylamino-phenylacetate, the following compounds can be prepared:
1-methyl-2-naphth-1'-yl-3-oxo-4-(3-trifluoromethylphenyl)-5-amino-4-pyrroline;
1-methyl-2-naphth-1'-ylmethylene-3-oxo-4-(3-trifluoromethylphenyl)-5-amino-4-pyrroline;
1-methyl-2-(3-fluorophenyl)-3-oxo-4-(3-trifluoromethylphenyl)-5-amino-4-pyrroline;
1-methyl-2-(3-trifluoromethylphenyl)-3-oxo-4-(3-trifluoromethylphenyl)-5-amino-4-pyrroline;
1-methyl-2-(2-methoxyphenyl)-3-oxo-4-(3-trifluoromethylphenyl)-5-amino-4-pyrroline;
1-methyl-2-(2-bromophenyl)-3-oxo-4-(3-trifluoromethylphenyl)-5-amino-4-pyrroline;
1-methyl-2-(3-methylphenyl)-3-oxo-4-(3-trifluoromethylphenyl)-5-amino-4-pyrroline;
1-methyl-2-(2-chloro-3-fluorophenyl)-3-oxo-4-(3-trifluoromethylphenyl)-5-amino-4-pyrroline;
1-methyl-2-(3-nitrophenyl)-3-oxo-4-(3-trifluoromethylphenyl)-5-amino-4-pyrroline;
1-methyl-2-ethyl-3-oxo-4-(3-trifluoromethylphenyl)-5-amino-4-pyrroline;
1-methyl-2-(2-fluoroethyl)-3-oxo-4-(3-trifluoromethylphenyl)-5-amino-4-pyrroline;
1-methyl-2-vinyl-3-oxo-4-(3-trifluoromethylphenyl)-5-amino-4-pyrroline;
1-methyl-2-(2-fluorovinyl)-3-oxo-4-(3-trifluoromethylphenyl)-5-amino-4-pyrroline; and
1-methyl-2-benzyl-3-oxo-4-(3-trifluoromethylphenyl)5-amino-4-pyrroline;
1-methyl-2-(2,5-dimethylphenyl)-3-oxo-4-(3-trifluoromethylphenyl)-5-amino-4-pyrroline;
1-methyl-2-(2-methoxy-3-methylphenyl)-3-oxo-4-(3-trifluoromethylphenyl)-5-amino-4-pyrroline;
1-methyl-2-methyl-3-oxo-4-(3-trifluoromethylphenyl)-5-amino-4-pyrroline.

Obviously, many modifications and variations of the invention described hereinabove and below can be made without departing from the essence and scope thereof.

What is claimed is:

1. A process for preparing substituted and unsubstituted aminoacetate esters having the formula:

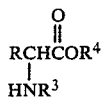

wherein R is hydrogen, lower alkyl having 1 through 6 carbon atoms; lower alkenyl having 2 through 6 carbon atoms; fluoroalkyl having 1 through 4 carbon atoms and 1 through 3 fluoro atoms; fluoroalkenyl having 2 through 4 carbon atoms and 1 through 3 fluoro atoms; phenyl; naphth-1-yl; 4-fluorophenyl, 2,6-difluorophenyl; benzyl; naphth-1-ylmethylene; 2-halobenzyl; 2-lower alkylbenzyl; 3-halobenzyl; 3-lower alkylbenzyl or substituted phenyl having the formula:

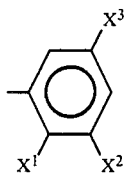

wherein
one or two of $X^1$, $X^2$ and $X^3$ is lower alkyl, lower alkoxy, halo, nitro, or haloalkyl having 1 through 3 carbon atoms and 1 through 3 of the same or different halo atoms and the remainder of $X^1$, $X^2$ and $X^3$ are hydrogen,
$R^3$ is methyl or ethyl and
$R^4$ is lower alkyl having 1 through 4 carbon atoms; which comprises contacting the corresponding haloacetate ester having the formula:

  (A)

wherein X is chloro, bromo, or iodo and R and $R^4$ are as defined hereinabove,
with the corresponding quaternary ammonium salt having the formula:

wherein $R^3$ is methyl or ethyl, M is an anion and m is its valence in a two-phase liquid-liquid reaction medium comprising water and a water immiscible inert organic solvent under reactive conditions in the presence of a phase transfer agent for transferring hydrophilic ions into liquid lipophilic organic mediums.

2. The process of claim 1 wherein said process is conducted at temperatures in the range of about from 0° to 100° C.

3. The process of claim 2 wherein said phase transfer agent is selected from the group of benzyl triethylammonium chloride, methyl trioctylammonium chloride, tetrabutyl ammonium chloride, tetrabutyl ammonium bromide, and compatible mixtures thereof.

4. The process of claim 1 wherein about from 0.05 to 1 mole equivalent of said phase transfer agent is used per mole of said haloacetate esters.

5. The process of claim 4 wherein X is bromo and M is chloride or bromide.

6. The process of claim 5 wherein said process is conducted at temperatures in the range of about from 40° C. to 45° C.

7. The process of claim 6 wherein said phase transfer agent is selected from the group of benzyl triethylammonium chloride, methyl trioctylammonium chloride, tetrabutyl ammonium chloride, tetrabutyl ammonium bromide, and compatible mixtures thereof.

8. The process of claim 7 wherein a water to said immiscible solvent volume ratio in the range of about from 1:10 to 1:15 is used.

9. The process of claim 8 wherein said immiscible solvent is selected from the group toluene and chloroalkanes having 1 or 2 carbon atoms and 1 through 3 chloro atoms, and mixtures thereof.

10. The process of claim 1 wherein X is bromo.

11. The process of claim 1 wherein said process is conducted for about from 1 to 60 hours.

12. The process of claim 1 wherein R is phenyl, naphth-1-yl, 4-fluorophenyl, 2,6-difluorophenyl or said substituted phenyl and wherein said process is conducted for about from 18 to 36 hours.

13. The process of claim 1 wherein R is hydrogen, lower alkyl, lower alkenyl, fluoromethyl, fluoroalkenyl, benzyl, naphth-1-ylmethylene, 2-halobenzyl, 2-lower alkylbenzyl, 3-halobenzyl or 3-lower alkylbenzyl and wherein said process is conducted for about from 24 to 48 hours.

14. The process of claim 1 wherein $R^4$ is methyl.

* * * * *